(12) United States Patent
Tonks et al.

(10) Patent No.: US 10,710,956 B2
(45) Date of Patent: Jul. 14, 2020

(54) PROCESS FOR THE PREPARATION OF ACRYLATE ESTERS FROM ALKYL LACTATES

(71) Applicant: Regents of the University of Minnesota, Minneapolis, MN (US)

(72) Inventors: Ian A. Tonks, Minneapolis, MN (US); Marc A. Hillmyer, Minneapolis, MN (US); Gereon M. Wuu-Yee, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 16/270,351

(22) Filed: Feb. 7, 2019

(65) Prior Publication Data
US 2019/0241495 A1 Aug. 8, 2019

Related U.S. Application Data

(60) Provisional application No. 62/628,140, filed on Feb. 8, 2018.

(51) Int. Cl.
| | | |
|---|---|---|
| *C07C 67/32* | (2006.01) | |
| *C07C 67/03* | (2006.01) | |
| *B01J 31/24* | (2006.01) | |
| *C07C 69/54* | (2006.01) | |
| *C07C 69/34* | (2006.01) | |
| *C07C 69/736* | (2006.01) | |

(52) U.S. Cl.
CPC ........... *C07C 67/32* (2013.01); *B01J 31/2404* (2013.01); *C07C 67/03* (2013.01); *B01J 2531/824* (2013.01); *C07C 69/34* (2013.01); *C07C 69/54* (2013.01); *C07C 69/736* (2013.01)

(58) Field of Classification Search
CPC ......... C07C 67/32; C07C 69/67; C07C 69/54; C07C 67/03; C07C 69/34; C07C 69/736; C07C 67/38; B01J 2531/824; B01J 21/2404
See application file for complete search history.

(56) References Cited

U.S. PATENT DOCUMENTS

| | | | |
|---|---|---|---|
| 2,265,814 A * | 12/1941 | Ritchie ........................ 558/379 |
| 2,859,240 A | 11/1958 | Holmen | |
| 4,729,978 A | 3/1988 | Sawicki | |
| 4,745,213 A | 5/1988 | Schlosser et al. | |
| 6,992,209 B2 | 1/2006 | Lilga et al. | |
| 9,056,829 B2 | 6/2015 | Parton et al. | |
| 9,290,430 B2 | 3/2016 | Fruchey et al. | |
| 9,670,134 B2 | 6/2017 | Sathiosatham et al. | |
| 2011/0065950 A1 | 3/2011 | Riisager et al. | |
| 2011/0097291 A1* | 4/2011 | Vial ...................... C11B 9/0019 424/65 |
| 2014/0155653 A1 | 6/2014 | Dongare et al. | |
| 2016/0194276 A1 | 7/2016 | Tolman et al. | |
| 2017/0022137 A1* | 1/2017 | Dong ...................... B01J 31/24 |
| 2017/0057900 A1 | 3/2017 | Velasquez et al. | |

OTHER PUBLICATIONS

Rehberg et al. (Preparation and Pyrolysis of Alkyl Alpha-Acetoxypropionates. Effect of Structure on Yield of Acrylic Ester, Published Jan. 1945. (Year: 1945).*
Kiss (Palladium-Catalyzed Reppe Carbonylation, Chem. Rev., 101, pp. 3435-3456, Published 2001) (Year: 2001).*
Blanco, E , et al., "Dehydration of ethyl lactate over alkaline earth phosphates: Performances, effect of water on reaction pathways and active sites", Applied Catalysis B: Environmental 180, 596-606 (2016).
Hillmyer, M , et al., "The promise of plastics from plants. Plant-derived feedstocks are increasingly competitive in plastics production", Science 358, 868-870 (2017).
John, A , et al., "Olefins from biomass feedstocks: catalytic ester decarbonylation and tandem Heck-type coupling", Chem Commun 51, 2731-2733 (2015).
John, A , et al., "Selective Decarbonylation of Fatty Acid Esters to Linear α-Olefins", Organometallics 36(15), 2956-2964 (2017).
Liu, J , et al., "Toward Green Acylation of (Hetero)arenes: Palladium-Catalyzed Carbonylation of Olefins to Ketones", ACS Cent Sci 4 (1), 30-38 (2018).
Miranda, M , et al., "Catalytic decarbonylation of biomass-derived carboxylic acids as efficient route to commodity monomers", Green Chemistry 14(2), 490-494 (2012).
Rehberg, C , et al., "Preparation and Pyrolysis of Alkyl Alpha-Acetoxypropionates, Etrect of Structure on Yield of Acrylic Ester", J Am Chem Soc 67, 56-57 (1945).
Roesle, P , et al., "Mechanistic Features of Isomerizing Alkoxycarbonylation of Methyl Oleate", J Am Chem Soc 134, 17696-17703 (2012).
Smith, L , et al., "Pyrolysis of Lactic Acid Derivatives. Conversion of Methyl a-Acetoxypropionate to Methyl Acrylate", Chemistry 34(4), 473-479 (1942).
Tang, C , et al., "Catalytic dehydration of lactic acid to acrylic acid over dibarium pyrophosphate", Catalysis Communications 43, 231-234 (2014).
Yan, B , et al., "Sustainable Production of Acrylic Acid: Catalytic Performance of Hydroxyapatites for Gas-Phase Dehydration of Lactic Acid", ACS Catal 4, 1931-1943 (2014).
Yee , et al., "Bioderived Acrylates from Alkyl Lactates via Pd-Catalyzed Hydroesterification", ACS Sustainable Chemistry & Engineering 6(8), 9579-9584 (2018).
Yee , et al., "Mechanistic Study of Palladium-Catalyzed Hydroesteritica-tive Copolymerization of Vinyl Benzyl Alcohol and CO", Organometallics 38(8), 1778-1786 (2019).

(Continued)

*Primary Examiner* — Yevgeny Valenrod
*Assistant Examiner* — Blaine G Doletski
(74) *Attorney, Agent, or Firm* — Viksnins Harris Padys Malen LLP

(57) ABSTRACT

Catalytic hydroesterification of alkyl lactates give alkyl 2-(propionyloxy)propanoates, starting from alkyl lactate, carbon monoxide, ethylene gas, and a palladium catalyst. Pyrolysis of alkyl 2-(propionyloxy)propanoates gives acrylate esters.

23 Claims, 8 Drawing Sheets

(56) References Cited

OTHER PUBLICATIONS

Zhang, J , et al., "Catalytic dehydration of lactic acid to acrylic acid over sulfate catalysts", Can J Chem Eng 86, 1047-1053 (2008).
Zhang, Z , et al., "Catalytic Performance and Characterization of Silica Supported Sodium Phosphates for the Dehydration of Methyl Lactate to Methyl Acrylate andAcrylic Acid", Ind Eng Chem Res 48, 9083-9089 (2009).

* cited by examiner

PROCESS FOR THE PREPARATION OF ACRYLATE ESTERS FROM ALKYL LACTATES

CROSS REFERENCE TO RELATED APPLICATION

This application claims priority to U.S. Provisional Application No. 62/628,140 filed on 8 Feb. 2018, which is incorporated by reference herein.

FIELD OF THE INVENTION

The present disclosure relates to methods of making acrylate esters from alkyl lactates through Pd-catalyzed hydroesterification with carbon monoxide and ethylene.

BACKGROUND

The global acrylic market is very large and it is expected to grow at a moderate rate to nearly 20 billion dollars per year by the end of the next decade at a CAGR (Compound Annual Growth Rate) of about 6%. The acrylic acid market by derivative type is segmented into acrylic esters, acrylic polymers, and other derivatives. The main driver of the market is the use of this precursor chemical in absorbent applications, with end-user markets in diapers, surface coatings, adhesives and sealants, plastic additive industry, water treatment industry, textiles, surfactants, and others. Currently, acrylic acid is heavily consumed in manufacturing diapers as polyacrylic acid and cross-linked polyacrylic acid, super absorbent polymers. Diapers are the fastest growing segment, at CAGR of 7.7%, and is expected to dominate the global acrylic acid market beyond 2020. Increasing geriatric population in the U.S. and Canada are projected to drive adult incontinence products demand. Geographically, the Asia Pacific market is projected to lead the global industry. Industrially important acrylate esters include methyl acrylate, butyl acrylate, ethyl acrylate, 2-ethylhexyl acrylate and others.

Inexpensive feedstocks derived from petrochemicals have sustained the production of plastic materials on a massive scale, but the limited nature of these resources has necessitated the development of synthetic routes derived from renewable resources. Stringent government regulations pertaining to the environmental safety and human health, and volatile prices of the raw materials are restricting the growth of the acrylate market globally. A key challenge lies not only in finding a viable route from renewable feedstocks, but also in developing an overall process that itself is sustainable, of low environmental impact, and economically competitive with traditional petroleum products (Hillmyer, M. A. *Science* (2017) 358:868-870). In this regard, lactic acid has shown particular promise given its ready availability from carbohydrates via fermentation (Bicker, M. et al, *J. Mol. Catal. A* (2005) 239:151; Holm, M. S. et al, *Science* (2010) 328:602; Kishida, H. et al, *Carbohydr. Res.* (2006) 341: 2619; Zeng, W. et al, *Catal. Lett.* (2009) 133:221; Rasrendra, C. B. et al, *J. Chem. Sus. Chem* (2011) 4:768) and its facile conversion into a number of commodity chemicals including polylactide (Mäki-Arvela, P. et al, *Chem. Rev.* (2014) 114: 1909-1971; Chen, G. Q. et al, *Chem. Rev.* (2012) 112:2082-2099).

Direct conversion of lactic acid and the corresponding alkyl lactates into acrylic acid and acrylate esters, respectively, has been reported (U.S. Pat. Nos. 2,859,240; 4,729, 978; US 2017/0057900; Zhang, J. et al, *Can. J. Chem. Eng.* (2008) 86:1047-1053; Zhang, Z. et al, *Ind. Eng. Chem. Res.* (2009) 48:9083-9089; US 2014/0155653; JP 2014189513 A; Tang, C. et al, *Catalysis Communications* (2014) 43:231-234; Blanco, E. et al, *Applied Catalysis B: Environmental* (2016) 180:596-606; Yan, B. et al, *ACS Catal.* (2014) 4:1931-1943). One such route is the direct dehydration of lactic acid using alkali and alkali earth metal catalysts (U.S. Pat. No. 5,252,473). However, these routes generally suffer from limited conversions and yields (Zhang, J. et al *ACS Catal.* (2011) 1:32; Sun, P. et al, *Ind. Eng. Chem. Res.* (2010) 49:9082; Ghantani, V. C. et al, *Green Chem.* (2013) 15:1211; Hong, J.-H. et al, *Appl. Catal., A* (2011) 396:194). Alternatively, pyrolysis of alkyl 2-acetoxy propanoate derivatives, which can be obtained from alkyl lactates directly by acetylation, also has been demonstrated to give the corresponding alkyl acrylates in varying yields with acetic acid as a coproduct (U.S. Pat. No. 2,477,293; Smith, L. T. et al, *Ind. Eng. Chem.* (1942) 34:473-479; Fisher, C. H. et al, *J. Am. Chem. Soc.* (1943) 65:763-767; Fein, M. L. et al, *J. Am. Chem. Soc.* (1944) 66:1201-1203; Filachione, E. M. et al, *J. Am. Chem. Soc.* (1944) 66:494-496; Fisher, C. H. et al, *Ind. Eng. Chem.* (1944) 36:229-234; Ratchford, W. P. et al, *Ind. Eng. Chem.* (1945) 37:382-387; Nezam, I. et al, *Org. Process Res. Dev.* (2017) 21:715-719). The nature of the alkyl (R) group of the starting lactate was shown to significantly affect the yield of the acrylate ester obtained (Burns, R. et al, *J. Chem. Soc.* (1935) 400-406; Rehberg, C. E. et al, *J. Am. Chem. Soc.* (1945) 67:56-57). Nickel catalyzed acetylation of lactide (the cyclic dimer of lactic acid) with acetic acid has been shown to give 2-acetoxypropionic acid, which can be subsequently pyrolyzed to give acrylic acid or converted to the methyl ester for production of methyl acrylate (U.S. Pat. No. 9,290,430). This route is attractive in that it gives high yields of acrylic acid or methyl acrylate from lactide, and utilizes readily available nickel(II) nitrate and nickel(II) acetate as the acetylation catalysts, but requires somewhat harsh conditions.

Currently, acrylic esters are derived from acrylic acid directly, which itself is produced from the oxidation of propene, a byproduct of ethylene and gasoline production, and requires expensive transition metal catalysts and high temperatures. Moving away from petroleum based feedstocks towards a biorenewable starting material is of key interest. The catalytic conversion of alkyl lactates into acrylate esters may have good potential for entry into the bio-renewable chemical commodity market. The shift away from petroleum chemical feedstock is an increasing driving force in the global market. Existing technologies can be complemented by the methods described herein.

SUMMARY

An aspect of the invention is a process for the preparation of an alkyl 2-(propionyloxy)propanoate of formula I:

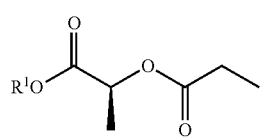

or a salt thereof, the process comprising contacting an alkyl lactate of formula II:

II

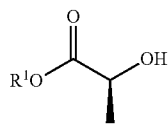

or a salt thereof, with carbon monoxide, ethylene, and a palladium compound under conditions sufficient to form an alkyl 2-(propionyloxy)propanoate of formula I;

wherein $R^1$ is selected from H, $C_1$-$C_{12}$ alkyl, and $C_6$-$C_{20}$ aryl, where alkyl and aryl are optionally substituted with one or more groups independently selected from F, Cl, Br, I, —CN, —$NH_2$, —$NHCH_3$, —$N(CH_3)_2$, —$NHS(O)_2CH_3$, —$NO_2$, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, and —$S(O)_3H$.

The process may further comprise heating the alkyl 2-(propionyloxy)propanoate ester of formula I or a salt thereof, to form an acrylate ester or acid of formula III:

III

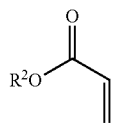

or a salt thereof, wherein $R^2$ is selected from H, $C_1$-$C_{12}$ alkyl, and $C_6$-$C_{20}$ aryl, where alkyl and aryl are optionally substituted with one or more groups independently selected from F, Cl, Br, I, —CN, —$NH_2$, —$NHCH_3$, —$N(CH_3)_2$, —$NHS(O)_2CH_3$, —$NO_2$, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, and —$S(O)_3H$;

and propionic acid or a salt thereof.

Another aspect of the invention is a hydroesterification process of converting an alkyl lactate of formula II to an alkyl 2-(propionyloxy)propanoate of formula I with carbon monoxide, ethylene, and a palladium catalyst.

Another aspect of the invention is a route from inexpensive and sustainably-produced lactic acid to acrylate esters by way of the palladium catalyzed hydroesterification of alkyl lactates (FIG. 1). Alkyl esters of lactic acid are carbonylated with carbon monoxide and ethylene to give the corresponding alkyl 2-(propionyloxy)propanoates, using a palladium catalyst. The catalytic species can be generated in situ in both neat alkyl lactate and organic solvent from cheap and readily available starting materials. The alkyl 2-(propionyloxy)propanoates give the corresponding acrylate esters and propionic acid upon pyrolysis. Further hydrolysis of the acrylate esters gives acrylic acid.

Another aspect of the invention is a process from bio-derived lactate esters to acrylic esters via a catalytic, two-step process performed under neat conditions, avoiding the need for solvent.

The methods of this disclosure are a significant improvement over older methods which rely on the acetylation of methyl lactate, which requires temperatures higher than 250 Celsius (° C.). Starting material lactic acid can be obtained from bio-renewable sources. Hydroesterification using CO and ethylene in presence of palladium catalyst is marked by relatively inexpensive reactants and low energy costs and produces a highly useful commodity chemical. This synthetic methodology has the additional advantage of having near-quantitative yield, which makes it ideal for scale-up use in industry.

DEFINITIONS

"Alkyl" as used herein refers to a saturated linear or branched-chain monovalent hydrocarbon radical of one to twelve carbon atoms ($C_1$-$C_{12}$), wherein the alkyl radical may be optionally substituted independently with one or more groups independently selected from F, Cl, Br, I, —CN, —NH$_2$, —NHCH$_3$, —N(CH$_3$)$_2$, —NHS(O)$_2$CH$_3$, —NO$_2$, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, and —S(O)$_3$H. In another embodiment, an alkyl radical is one to eight carbon atoms ($C_1$-$C_8$), or one to six carbon atoms ($C_1$-$C_6$), or one to four carbon atoms ($C_1$-$C_4$). Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$) CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH (CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH (CH$_3$)CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$ CH$_2$CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$), 3,3-dimethyl-2-butyl (—CH(CH$_3$)C (CH$_3$)$_3$, 1-heptyl, and 1-octyl.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

DESCRIPTION

Figure 1:
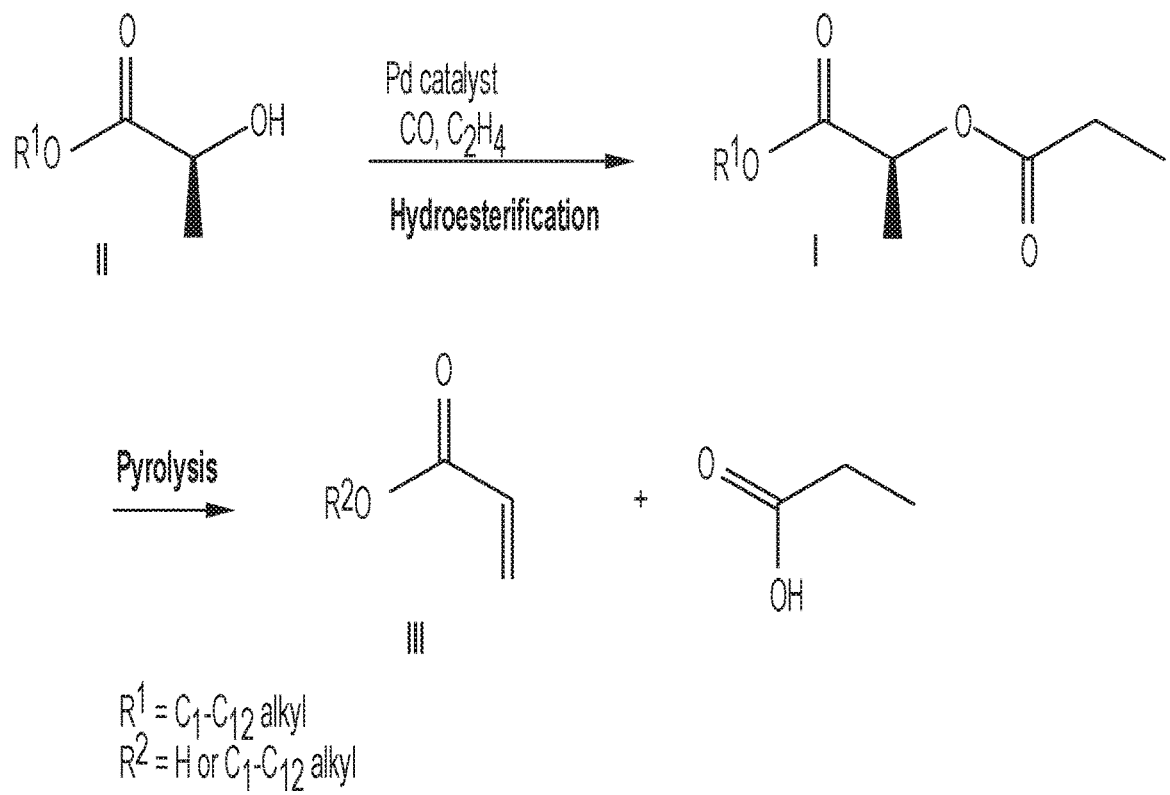
FIG. 1 shows a process route to acrylate esters III from alkyl lactates II by hydroesterification of II with carbon monoxide, ethylene, and a palladium catalyst to form a alkyl 2-(propionyloxy)propanoate I followed by pyrolysis of I to form III, acrylic acid (R=H), and propionic acid. The (S) isomers of I and II are depicted, although the process also contemplates the use of the (R) isomers, as well as racemates and all other stereoisomeric mixtures.

A process for the conversion of alkyl lactates II to their corresponding alkyl 2-(propionyloxy)propanoates I ($R^1$=$C_1$-$C_{12}$ alkyl) by way of palladium-catalyzed hydroesterification with carbon monoxide, CO and ethylene, $C_2H_4$ (FIG. 1) is provided. The (S) isomers of I and II are depicted, although the process also contemplates the use of the (R) isomers, as well as racemates and all other stereoisomeric mixtures.

The process utilizes inexpensive starting materials and produces acrylate esters III ($R^2$=$C_1$-$C_{12}$ alkyl), acrylic acid ($R^2$=H) and propionic acid as useful coproducts upon pyrolysis of the alkyl 2-(propionyloxy)propanoates I.

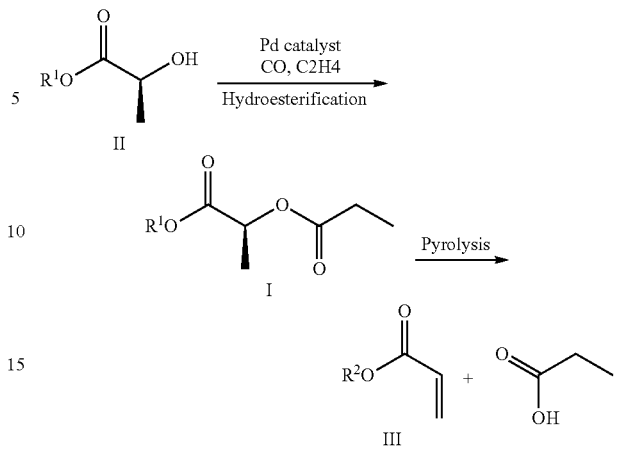

In an exemplary embodiment, $R^1$ is hydrogen.
In an exemplary embodiment, $R^1$ is methyl.
In an exemplary embodiment, $R^1$ is ethyl.
In an exemplary embodiment, $R^1$ is phenyl.
In an exemplary embodiment, the palladium compound is present at a catalytic amount in the range of 0.5 to 4%.

In an exemplary embodiment, the palladium compound is selected from Pd(OAc)$_2$, Pd(OTs)$_2$(MeCN)$_2$, Pd(OCOCF$_3$)$_2$, Pd(BF$_4$)$_2$(MeCN)$_2$, Pd(BAr$^F$$_4$)$_2$(MeCN)$_2$, Pd(PF$_6$)$_2$(MeCN)$_2$, PdX$_2$ (X=Cl, Br, I), and Pd(OTf)$_2$ (MeCN)$_2$.

In an exemplary embodiment, the alkyl lactate of formula II, carbon monoxide, ethylene, and palladium compound are contacted at a pressure in the range of 14.7 to 1000 psig of carbon monoxide.

In an exemplary embodiment, the alkyl lactate of formula II, carbon monoxide, ethylene, and a palladium compound are at a pressure in the range of 14.7 to 1000 psig of ethylene.

In an exemplary embodiment, the alkyl lactate of formula II, carbon monoxide, ethylene, and a palladium compound are at a total pressure in the range of 29.4 to 2000 psig.

In an exemplary embodiment, the conditions of contacting the alkyl lactate of formula II with carbon monoxide, ethylene, and a palladium compound are at a temperature in the range of 20 to 150° C.

In an exemplary embodiment, the conditions of contacting the alkyl lactate of formula II with carbon monoxide, ethylene, and a palladium compound further comprises a solvent selected from toluene, DMF, acetonitrile, THF, ethyl acetate, nitromethane, N-methyl pyrrolidinone, and 2-MeTHF.

In an exemplary embodiment, the conditions of contacting the alkyl lactate of formula II with carbon monoxide, ethylene, and a palladium compound do not include a solvent wherein the reaction is conducted neat.

In an exemplary embodiment, the conditions of contacting the alkyl lactate of formula II with carbon monoxide, ethylene, and a palladium compound further comprises a phosphine reagent.

In an exemplary embodiment, the phosphine reagent is selected from the group consisting of triphenylphosphine, P(tBu)$_3$, P(o-Tol)$_3$, dppf, and dppe.

In an exemplary embodiment, the conditions of contacting the alkyl lactate of formula II with carbon monoxide, ethylene, and a palladium compound further comprises an organic acid selected from para-toluene sulfonic acid, methanesulfonic acid, trifluoromethane sulfonic acid, acetic acid, and trifluoroacetic acid; or an inorganic acid selected from hydrochloric acid, sulfuric acid, tetrafluoroboric acid, hexafluorophosphoric acid, and tetrakis(bis(3,5-trifluoromethyl)phenyl)boric acid.

In an exemplary embodiment, $R^2$ is H.
In an exemplary embodiment, $R^2$ is methyl.
In an exemplary embodiment, $R^2$ is ethyl.
In an exemplary embodiment, $R^2$ is phenyl.
In an exemplary embodiment, the alkyl 2-(propionyloxy)propanoate ester of formula I is heated at a temperature in the range of 450 to 600° C.

In an exemplary embodiment, the alkyl 2-(propionyloxy)propanoate ester I is passed through the inlet of a heating unit and exited into a collector vessel, wherein the heating unit is heated at about 500° C.

In an exemplary embodiment, the alkyl 2-(propionyloxy)propanoate ester of formula I is passed through the heating unit with a carrier gas selected from the group consisting of nitrogen, argon, helium, and carbon dioxide.

In an exemplary embodiment, the heating unit is a pyrex glass or quartz tube.

In an exemplary embodiment, the collector vessel is cooled below ambient temperature.

In an exemplary embodiment, the alkyl 2-(propionyloxy)propanoate ester I is heated for about one second to about 45 seconds.

In an exemplary embodiment, $R^2$ is H and the salt of acrylic acid is selected from sodium, potassium, and ammonium.

In an exemplary embodiment, the salt of propionic acid is selected from sodium, potassium, and ammonium.

Hydroesterification

The conversion of methyl lactate 1a and ethyl lactate 1b to their corresponding alkyl 2-(propionyloxy)propanoate esters 2a and 2b, respectively, was achieved by palladium catalyzed hydroesterificative coupling with carbon monoxide (CO) and ethylene at moderate temperatures and CO pressures. A screening of reaction conditions showed that the reaction could be conducted at low loadings of palladium catalyst, which was generated in situ from inexpensive and commercially available reagents. High conversions and product yields were obtained in a variety of solvents and even under neat conditions. Product analysis identified transesterification to be the primary competing reaction, which could be mitigated by changing solvents, as well as minimizing the amount of excess acid present in solution. Pyrolysis of methyl and ethyl 2-(propionyloxy)propanoate 2a and 2b, transformed these esters into their respective acrylates III, suitable for subsequent polymerization.

Methyl and ethyl lactate are efficiently converted to the corresponding alkyl 2-(propionyloxy)propanoates via catalytic hydroesterification at moderate reaction temperatures, and moderate pressures of ethylene and carbon monoxide. The reactions proceed at relatively low Pd loadings, and the formation of transesterification side products can be significantly mitigated by reducing the presence of excess acid. These reactions can also be effectively carried out under neat conditions. Pyrolytic decomposition of the corresponding propanoate esters has shown that the desired acrylate esters are indeed products in these reactions, with the methyl ester giving a more favorable yield of product, in line with previous studies of the alkyl 2-acetoxypropanoates.

The palladium-catalyzed hydroesterification process proceeds at moderate temperatures (80-120° C.), and may be carried out under neat and acid-free conditions (Brennfuehrer, A. et al, *Chem. Cat. Chem.* (2009) 1:28-41; Li, H. et al, *Nat. Chem.* (2016) 8:1159-1166; Dong, K. et al, *Angew. Chem., Int. Ed.* (2017) 56:5267-5271; Wu, X.-F. et al, *Chem. Rev.* (2013) 113:1-35).

The palladium-catalyzed hydroesterification process may allow for the possible installation of greater chemical complexity at the formed ester group (Larsen, M. B. et al, *ACS Macro. Lett.* (2018) 7:122-126; U.S. Pat. Nos. 9,505,778; 9,127,113; 8,420,704), and the potential to further optimize the pyrolysis reaction, and thus the coproducts generated.

Figure 3:
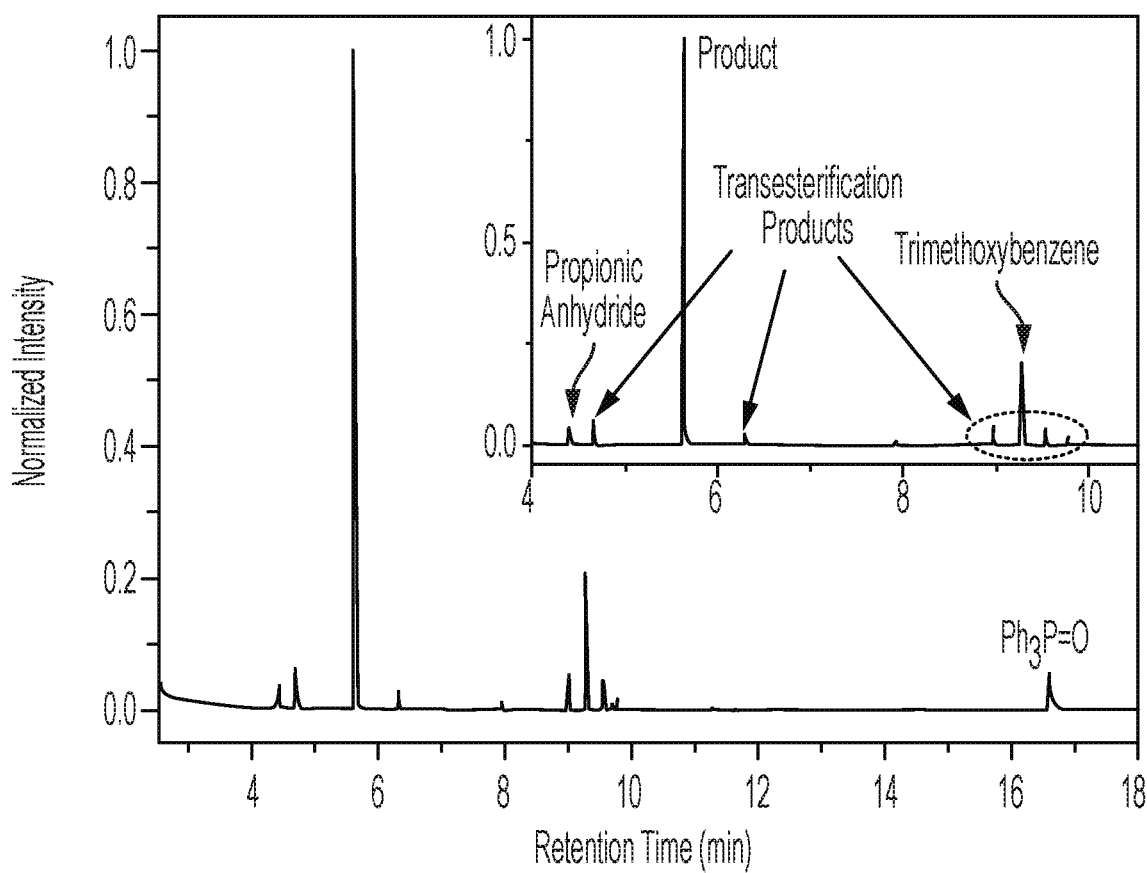
FIG. 3 shows a representative gas chromatography-flame ionization detector (GC-FID) chromatogram of the reaction mixture corresponding to entry 2 in Table 1.
Figure 6:
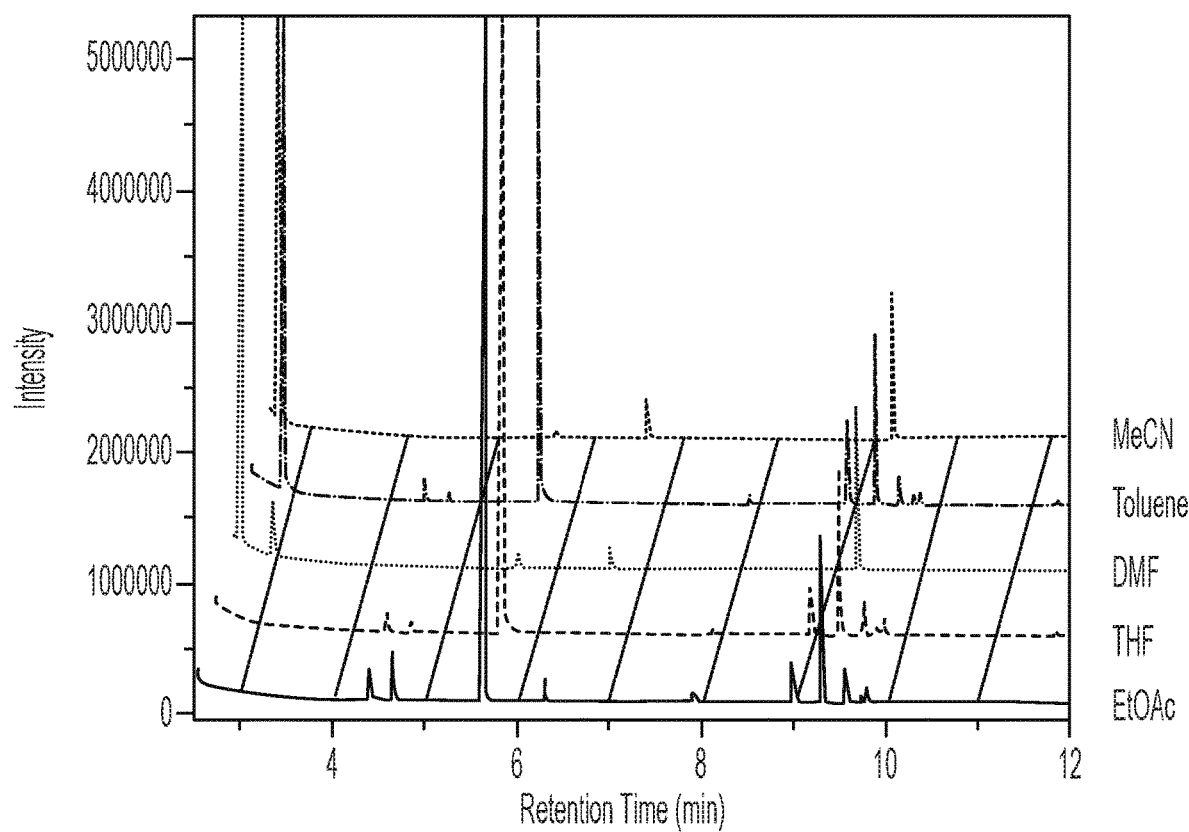
FIG. 6 shows the overlay of GC-FID chromatograms of reaction mixtures for the hydroesterification of methyl lactate run in five different solvents, from top to bottom: acetonitrile, toluene, dimethylformamide (DMF), tetrahydrofuran (THF), and ethylacetate (EtOAc) to illustrate the effect of reaction solvent on conversion of 1a (RT=2.61 min), formation of 2a (RT=5.63 min), and side product formation.

In exemplary embodiments, palladium catalyzed hydroesterification of methyl and ethyl lactate (1a and 1b, respectively) gave the corresponding alkyl 2-(propionyloxy)propanoates (2a and 2b), utilizing a simple and robust catalyst system. Pyrolytic decomposition of 2a and 2b gave methyl and ethyl acrylate as products of these reactions (Example 2). The hydroesterification reaction outlined in FIG. 1 and detailed in Example 1 was attempted with a catalyst loading of 1% Pd(OAc)$_2$/4% para-toluenesulfonic acid hydrate, TsOH·H$_2$O/16% PPh$_3$, and 80 psig of both CO and C$_2$H$_4$ (total pressure=160 psig). An initial solvent screen of toluene, DMF, MeCN, THF, and EtOAc showed that for a 16 h reaction, conversions of 1a to 2a are high in toluene, THF, and EtOAc (FIG. 6) and lead to the formation of a single major product as indicated by GC-FID analysis (FIG. 3, retention time=5.61 min) of the reaction mixture corresponding to entry 2 in Table 1 (1% Pd(OAc)$_2$, 4% TsOH·H$_2$O, 16% PPh$_3$). Minor amounts of propionic anhydride and transesterification products were also observed. A known amount of trimethoxybenzene was added for quantitative calibration.

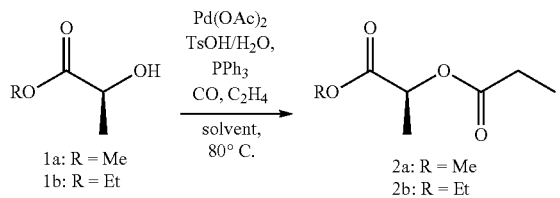

1a: R = Me
1b: R = Et

2a: R = Me
2b: R = Et

Figure 7A:
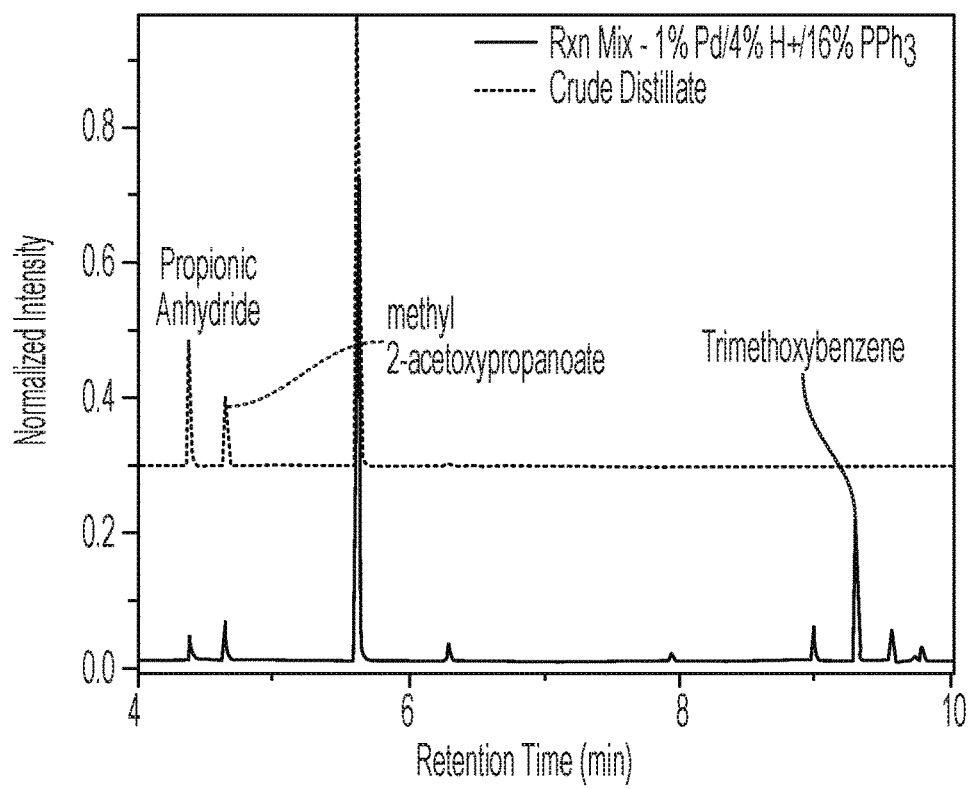
FIG. 7A shows a stack of GC-FID chromatograms: (bottom) reaction mixture of entry 2 of Table 1, hydroesterification of methyl lactate 1a with 1% $Pd(OAc)_2$, 4% TsOH·$H_2O$, 16% $PPh_3$, showing the major product, methyl 2-(propionyloxy)propanoate 2a, and (top) crude distillate of the reaction mixture showing 2a, along with propionic anhydride and methyl 2-acetoxypropanoate. Trimethoxybenzene is added to the reaction mixture sample for quantitation.

Vacuum distillation afforded a colorless oil. Analysis of this product by $^1$H NMR spectroscopy was consistent with methyl 2-(propionyloxy)propanoate 2a by comparison with an authentic sample prepared by the methods of Example 3. Additional minor peaks were also observed in the chromatogram of the reaction mixture, which upon isolation and independent synthesis were shown to correspond to products resulting from the transesterification of 1a with EtOAc to give the corresponding acetate of 1a (and presumably ethanol), as well as the self-condensation of 1a to give methyl lactate oligomers. FIG. 7A shows a stack of GC-FID chromatograms: (bottom) reaction mixture of entry 2 of Table 1, hydroesterification of methyl lactate 1a with 1% Pd(OAc)$_2$, 4% TsOH·H$_2$O, 16% PPh$_3$, showing the major product, methyl 2-(propionyloxy)propanoate 2a, and (top) crude distillate of the reaction mixture showing 2a is readily isolated by vacuum distillation, along with propionic anhydride and methyl 2-acetoxypropanoate. Trimethoxybenzene was added to the reaction mixture sample for quantitation.

Figure 7B:
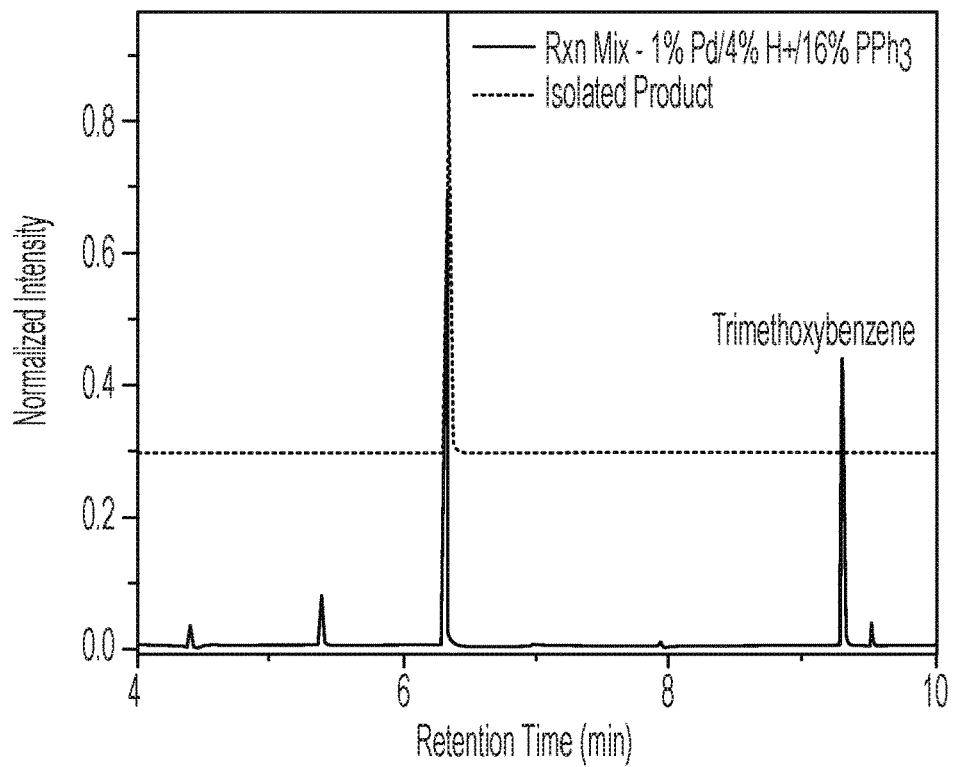
FIG. 7B shows a stack of GC-FID chromatograms: (bottom) reaction mixture of entry 2 of Table 2, hydroesterification of ethyl lactate 1b with 1% $Pd(OAc)_2$, 4% TsOH·$H_2O$, 16% $PPh_3$, showing the major product, ethyl 2-(propionyloxy)propanoate 2b, and (top) product 2b isolated by vacuum distillation.

By analogy, reactions with ethyl lactate 1b also lead to the formation of the desired ethyl 2-(propionyloxy)propanoate 2b as the major product, structure confirmed by comparison with an authentic sample prepared by the methods of Example 4. FIG. 7B shows a stack of GC-FID chromatograms: (bottom) reaction mixture of entry 2 of Table 2, hydroesterification of ethyl lactate 1b with 1% Pd(OAc)$_2$, 4% TsOH·H$_2$O, 16% PPh$_3$, showing the major product, ethyl 2-(propionyloxy)propanoate 2b, along with propionic anhydride and methyl 2-acetoxypropanoate and (top) product 2b isolated by vacuum distillation.

Catalyst loadings were varied to determine the effect of each component of the catalyst system on the conversions of 1a and 1b, as well as the yields of 2a and 2b and their respective side-products (Tables 1 and 2). From entries 1-6 in both tables, it can be seen that Pd loadings ranging from 0.5-4% give moderate to high conversions of substrate over a 16 h reaction period, and that between about 30-50% of the substrate is consumed within 4 h. Increasing the Pd concentration generally leads to higher yields of 2a and 2b and decreased side-product formation.

TABLE 1

Effect of Pd(OAc)$_2$, TsOH•H$_2$O, and PPh$_3$ loadings on conversion of methyl lactate (1a) to methyl 2-(propionyloxy)propanoate (2a).[a]

| Entry | Pd/H$^+$/L (%) | Time (hrs) | Conversion (%)[b] | Product Yield (%)[b] | Transester Yield (%)[b] |
|---|---|---|---|---|---|
| 1 | 0.5/4/16 | 16 | 77 | 48 | 25 |
| 2 | 1/4/16 | 16 | >99 | 79 | 7 |
| 3 | 4/4/16 | 16 | 68 | 56 | 7 |
| 4 | 0.5/4/16 | 4 | 48 | 24 | 18 |
| 5 | 1/4/16 | 4 | 53 | 47 | 6 |
| 6 | 4/4/16 | 4 | 34 | 31 | 5 |
| 7 | 1/0.5/16 | 4 | 4 | 0 | 1 |
| 8 | 1/1/16 | 4 | 13 | 7 | 2 |
| 9 | 1/16/16 | 4 | >99 | 32 | 34 |
| 10[c] | 1/4/0.5 | 4 | 72 | <1 | 55 |
| 11[c] | 1/4/1 | 4 | 72 | <1 | 50 |
| 12[c] | 1/4/4 | 4 | 26 | 8 | 10 |

[a]10.47 mmol substrate (1 mL), Solvent = EtOAc (2 mL), Pd = Pd(OAc)$_2$, H$^+$ = TsOH•H$_2$O, L = PPh$_3$.
[b]Conversion and yields based on GC-FID quantitation with trimethoxybenzene as an internal standard.
[c]Significant formation of Pd black.

TABLE 2

Effect of Pd(OAc)$_2$, TsOH•H$_2$O, and PPh$_3$ loadings on conversion of ethyl lactate (1b) to ethyl 2-(propionyloxy)propanoate (2b).[a]

| Entry | Pd/H$^+$/L (%) | Time (hrs) | Conversion (%)[b] | Product Yield (%)[b] | Transester Yield (%)[b] |
|---|---|---|---|---|---|
| 1[c] | 0.5/4/16 | 16 | >99 | 80 | 13 |
| 2[c] | 1/4/16 | 16 | >99 | 91 | 7 |
| 3[c] | 4/4/16 | 16 | 94 | 84 | 7 |
| 4 | 0.5/4/16 | 4 | 31 | 13 | 10 |
| 5 | 1/4/16 | 4 | 44 | 31 | 5 |
| 6 | 4/4/16 | 4 | 61 | 48 | 4 |
| 7 | 1/0.5/16 | 4 | 15 | 2 | <1 |
| 8 | 1/1/16 | 4 | 13 | 5 | <1 |
| 9 | 1/16/16 | 4 | 65 | 19 | 22 |
| 10[c] | 1/4/0.5 | 4 | 26 | 1 | 15 |
| 11[c] | 1/4/1 | 4 | 21 | 3 | 15 |
| 12[c] | 1/4/4 | 4 | 19 | 13 | 5 |

[a]8.72 mmol substrate (1 mL), Solvent = EtOAc (2 mL), Pd = Pd(OAc)$_2$, H+ = TsOH•H2O, L = PPh3.
[b]Conversion and yields based on GC-FID quantitation with trimethoxybenzene as an internal standard.
[c]Significant formation of Pd black.

However, conversion of 1a and yield of 2a drops off as the Pd loading is increased from 1-4% which may be due in part to a sub-stoichiometric amount of acid at the higher Pd concentration (vida infra). This behavior was not observed for reactions with 1b, and it is not immediately clear why. Additionally, it was observed that during reactions with both 1a and 1b, higher Pd loadings lead to the formation of a significant amount of yellow precipitate over the course of the reaction. This species, characterized as (Ph$_3$P)$_4$Pd$_3$(CO)$_3$ by $^{31}$P NMR and X-ray crystallography, does not appear to be active in the catalytic cycle, and suggests that a significant portion of the catalyst deactivates under these conditions.

Varying the loadings of TsOH·H$_2$O and PPh$_3$ both dramatically affect the conversion of substrate, and importantly the yields of 2a/2b relative to their side-products. In both cases, transesterification dominates the consumption of substrate at low TsOH·H$_2$O and PPh$_3$ loadings, and only once the optimum loading is reached does production of 2a/2b out-compete side product formation. This behavior is attributed to the fact that active catalyst formation is severely limited at low loadings of either TsOH·H$_2$O or PPh$_3$, giving low product yields, whereas increasing the TsOH·H$_2$O and PPh$_3$ loadings to 4% and 16%, respectively, results in more complete conversion of Pd(OAc)$_2$ to a putative [Pd—H]$^+$ intermediate (FIG. 2), and thus high conversions and yields. Increasing the acid loading above 4% results in sharp drops to both conversion and yield of 2a as the excess acid promotes more facile transesterification. Thus, some amount of excess acid is beneficial in promoting catalysis, but too much leads to increased side-product formation.

Figure 9A:
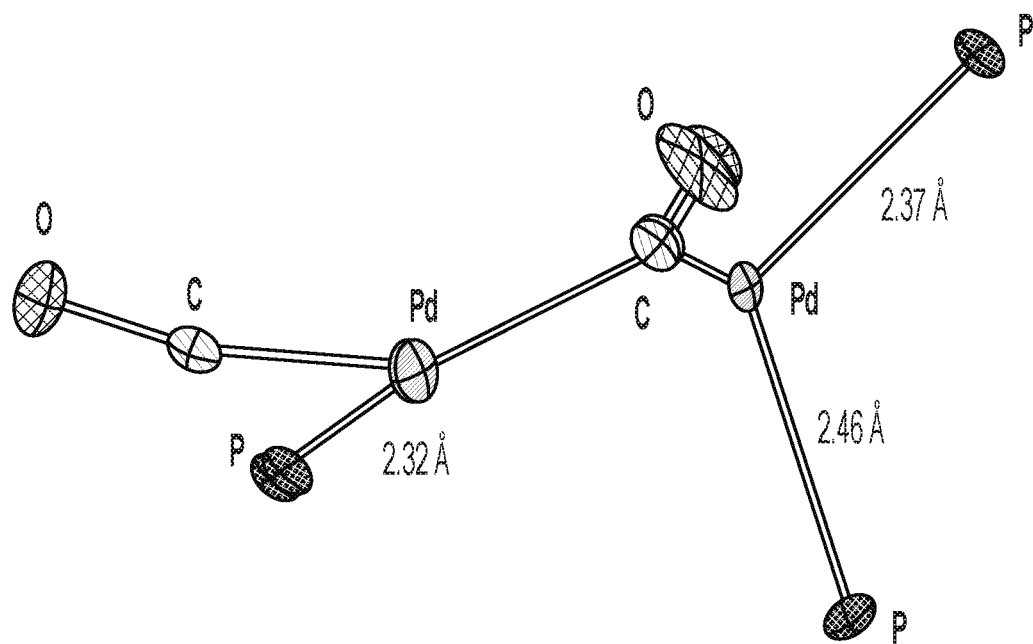
FIG. 9A shows an X-ray crystal structure obtained of yellow crystalline material isolated from crude hydroesterification reactions of methyl and ethyl lactate. Ellipsoids represent C, O, Pd, and P atoms, and are drawn at the 50% probability level. H-atoms and phosphorus substituents are omitted for clarity.
Figure 9B:
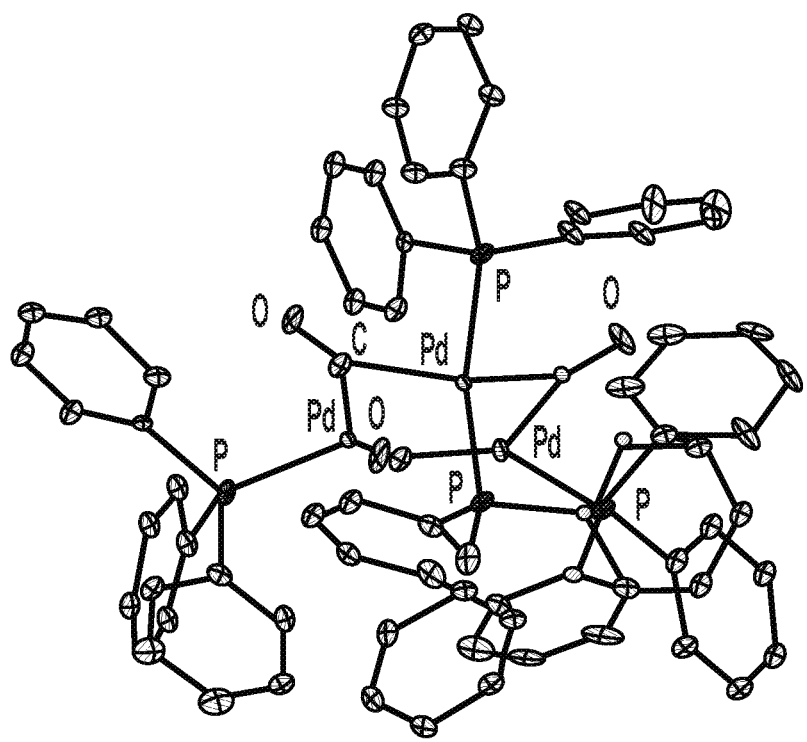
FIG. 9B shows an X-ray crystal structure obtained of yellow crystalline material isolated from crude hydroesterification reactions of methyl and ethyl lactate. Ellipsoids represent C, O, Pd, and P atoms, and are drawn at the 50% probability level. H-atoms omitted for clarity. The orientation of triphenylphosphine ligands are shown.

FIGS. 9A and 9B show the X-ray crystal structure obtained of yellow crystalline material isolated from crude hydroesterification reactions of methyl and ethyl lactate. Ellipsoids represent C, O, Pd, and P atoms, and are drawn at the 50% probability level. H-atoms omitted for clarity. FIG. 9A shows phosphorus substituents omitted for clarity. FIG. 9B shows the orientation of triphenylphosphine ligands. The unit cell matched that of a previous report of this structure (Mednikov, E. G. et al, Koord. Khim. (1987) 13:979-985).

Figure 2:
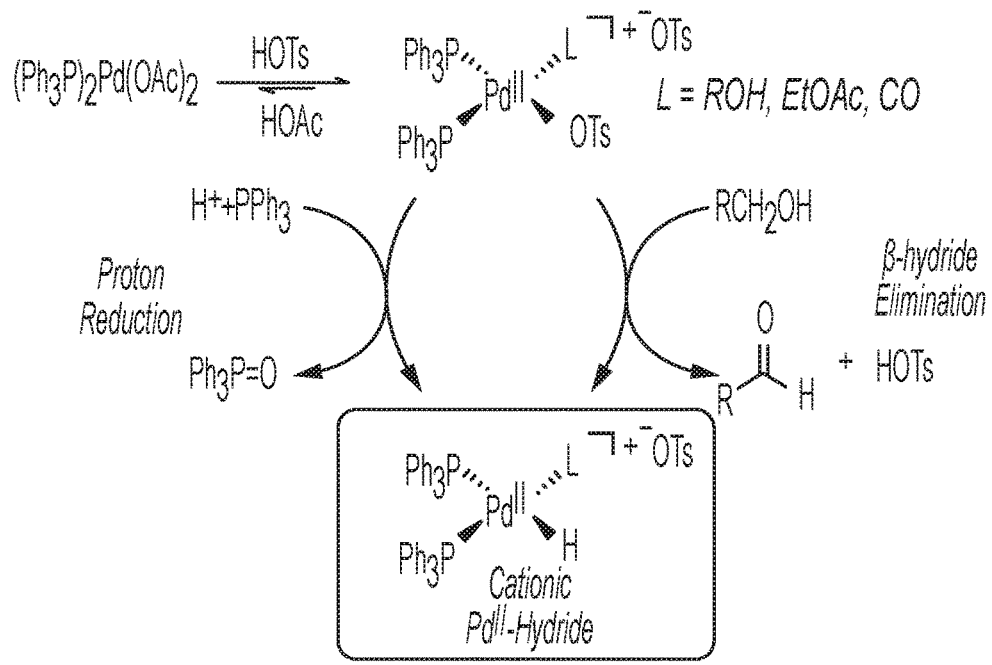
FIG. 2 shows putative formation of the active [Pd—H]$^+$ intermediate formed during hydroesterification.

An acid free catalyst system was developed to mitigate the formation of transesterification products. The catalyst Pd(OTs)$_2$(MeCN)$_2$ (Drent, E. et al, J. Organomet. Chem. (1991) 417:235-251.) was employed as Pd source, and the results of these reactions are given in Table 3. As expected, transesterification products were absent. Notably, these reactions seemed to progress more slowly than the analogous reactions with Pd(OAc)$_2$ and TsOH·H$_2$O; 16 h did not give full conversion of substrate. Given these results, and the low conversion observed for entry 3 of Table 1, it appears that exogenous TsOH plays a role in promoting higher substrate conversion in reactions with 1a, likely by facilitating more rapid generation of a [Pd—H]$^+$ intermediate (FIG. 2). While formation of the palladium hydride species (Roesle, P. et al, J. Am. Chem. Soc. (2012) 134:17696-17703) is generally proposed to occur via oxidation of the alcoholic substrate (Witt, T. et al, ACS Catal. (2015) 5:4519-4529) the electron deficient nature of the alcohol in this system may slow down this process, resulting in a greater contribution from the proton reduction pathway (FIG. 2). This pathway has been implicated in related hydro-arylation reactions, for which formation of the active hydride species by substrate oxidation is not possible (Liu, J. et al, ACS Cent. Sci. (2017) DOI: 10.1021/acscentsci.7b00368). Indeed, repeating the reaction with 1% Pd(OTs)$_2$(MeCN)$_2$ and 1% or 4% TsOH·H$_2$O led to full conversion of substrate over the same time period with a virtually negligible increase in the formation of transesterification products in the former case (Table 3). As observed for the Pd(OAc)$_2$/TsOH system, too much exogenous acid promotes transesterification and leads to reduced product yields (entry 5). Full substrate conversions and moderate to high yields of 2a were also achieved under neat conditions (Table 4) utilizing this strategy.

TABLE 3

Effect of Pd(OTs)$_2$(MeCN)$_2$ and TsOH•H$_2$O loadings on conversion of methyl lactate (1a) to methyl 2-(propionyloxy)propanoate (2a).[a]

| Entry | Pd/H$^+$/L (%) | Conversion (%)[b] | Product Yield (%)[b] | Byproduct Yield (%)[b] |
|---|---|---|---|---|
| 1 | 0.5/0/16 | 30 | 15 | 2 |
| 2 | 1/0/16 | 62 | 47 | 1 |
| 3 | 4/0/16 | 85 | 78 | 1 |
| 4 | 1/1/16 | 98 | 91 | 2 |
| 5 | 1/4/16 | >99 | 75 | 11 |

[a]10.47 mmol substrate (1 mL), 16 h reaction time, Solvent = EtOAc (2 mL), H$^+$ = TsOH•H$_2$O, L = PPh$_3$.
[b]Conversion and yields based on GC-FID quantitation with trimethoxybenzene as an internal standard.

TABLE 4

Substrate conversions and product yields for reactions run in neat methyl lactate.[a]

| Entry | Pd/H$^+$/L (%) | Conversion (%)[b] | Product Yield (%)[b] | Byproduct Yield (%)[b] |
|---|---|---|---|---|
| 1 | 1/0/16[c] | 62 | 47 | 1 |
| 2 | 1/1/16[c] | 95 | 66 | 1 |
| 3 | 1/4/16[d] | 99 | 84 | 1 |

[a]10.47 mmol substrate (1 mL), 16 h reaction time, H$^+$ = TsOH•H$_2$O, L = PPh$_3$.
[b]Conversion and yields based on GC-FID quantitation with trimethoxybenzene as an internal standard.
[c]Pd = Pd(OTs)$_2$(MeCN)$_2$.
[d]Pd = Pd(OAc)$_2$ While palladium acetate, Pd(OAc)$_2$ (CAS Reg. No. 003375-31-3) is an effective catalyst or catalyst precursor for the reaction, other types of palladium catalysts or catalyst precursors can also be used. The active Pd—H intermediate is a Pd(II) species, potentially formed from a Pd(0) species. 1,1'-Bis(diphenylphosphino)ferrocene (dppf), is an organophosphorus compound commonly used as a ligand in homogeneous catalysis. Nonlimiting examples of palladium catalysts or catalyst precursors include PdCl$_2$(dppf), Pd$_2$(dba)$_3$, and Na$_2$PdCl$_4$. While dppf is an effective ligand for the reaction, other types of ligands (monodentate or bidentate) can also be used. Nonlimiting examples of such ligands include P(t-Bu)$_3$, P(o-Tol)$_3$, as well as nonphosphorous ligands. Without being limited to a particular mechanism of action, the active catalyst can be generated by using a Pd(0) source such as Pd$_2$(dba)$_3$ or Pd(PPh$_3$)$_4$ and a mono or bidentate ligand such as PR$_3$ or dppf (and others) or a Pd(0) species can be generated in situ from a Pd(II) source such as Pd(OAc)$_2$, Na$_2$PdCl$_4$ with a mono or bidentate phosphine such as PPh$_3$, P(t-Bu)$_3$, P(o-Tol)$_3$, dppf, dppe (1,2-diphenylphosphinoethane).

Other types of palladium catalysts or catalyst precursors may be useful for the hydroesterification reaction such as PdCl$_2$(PPh$_3$)$_2$, Pd(t-Bu)$_3$, PdCl$_2$ dppf CH$_2$Cl$_2$, Pd(PPh$_3$)$_4$, Pd(OAc)/PPh$_3$, Cl$_2$Pd[(PEt$_3$)]$_2$, Pd(DIPHOS)$_2$, Cl$_2$Pd (Bipy), [PdCl(Ph$_2$PCH$_2$PPh$_2$)]$_2$, Cl$_2$Pd[P(o-tol)$_3$]$_2$, Pd$_2$(dba)$_3$/P(o-tol)$_3$, Pd$_2$(dba)/P(furyl)$_3$, Cl$_2$Pd[P(furyl)$_3$]$_2$, Cl$_2$Pd(PMePh$_2$)$_2$, Cl$_2$Pd[P(4-F-Ph)$_3$]$_2$, Cl$_2$Pd[P(C$_6$F$_6$)$_3$]$_2$, Cl$_2$Pd[P(2-COOH-Ph)(Ph)$_2$]$_2$, Cl$_2$Pd[P(4-COOH-Ph)(Ph)$_2$]$_2$, and encapsulated catalysts Pd EnCat™ 30, Pd EnCat™ TPP30, and Pd(II)EnCat™ BINAP30, according to procedures analogous to those described in J. Tsuji, "Transition Metal Reagents and Catalysts, Innovations in Organic Synthesis", John Wiley & sons, Chichester, 2000 and references cited therein. Palladium catalyzed reactions may be conducted in the presence of organic solvents such as acetonitrile (MeCN), tetrahydrofuran (THF), tert-butylmethyl ether, 2-methyltetrahydrofuran (2-MeTHF), dibutyl ether, cyclopentylmethyl ether, dimethyl acetal or dioxane, N,N-dimethylformamide (DMF) and N-methylpyrrolidone (NMP), and with bases such as K$_3$PO$_4$, K$_2$CO$_3$, KHCO$_3$, Cs$_2$CO$_3$, KOH, NaOH, trimethylamine, tripropylamine, pyridine, N,N-diethylpropylamine, N,N-diisopropylethylamine, and N-methylmorpholine.

Pyrolysis

Figure 5:
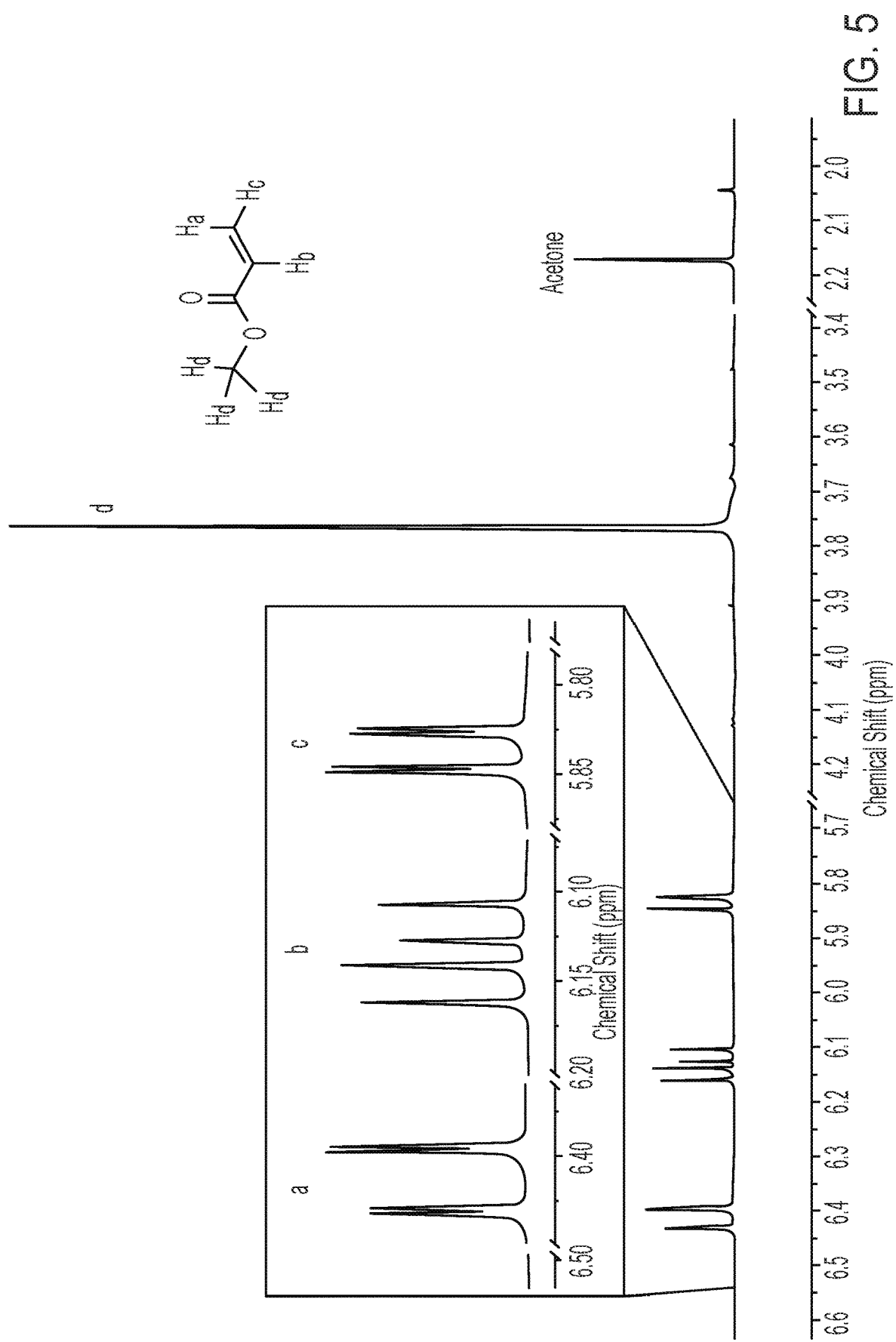
FIG. 5 shows the $^1$H NMR spectrum (500 MHz, $CDCl_3$) of crude oil obtained from pyrolysis of methyl 2-(propionyloxy)propanoate.

Compounds 2a and 2b are thus prepared in very high yields using low levels of Pd and easily isolated by distillation. Pyrolysis of these propionate esters were investigated to determine if they would also result in alkyl acrylate formation as in the case of the acetoxy esters (Filachione, E. M. et al, *J. Am. Chem. Soc.* (1944) 66:494-496; Fisher, C. H. et al, *Ind. Eng. Chem.* (1944) 36:229-234; Ratchford, W. P. et al, *Ind. Eng. Chem.* (1945) 37:382-387; Nezam, I. et al, *Org. Process Res. Dev.* (2017) 21:715-719). Methyl 2-(propionyloxy)propanoate 2a was volatilized at about 250° C. and passed through a pyrex tube packed with borosilicate beads/cylinders which had been heated to about 500-550° C. (Example 2). A light yellow oil was collected in the first of two receiving flasks which were cooled in dry-ice/isopropanol baths. The $^1$H NMR spectrum of the oil was very clean, clearly displaying the characteristic alkene doublet-of-doublets (FIG. 5) for methyl acrylate. Another product from this reaction is propionic acid, which due to the design of the pyrolysis apparatus, condensed in the pyrolysis tube before it had a chance to reach the collection flask. The rough isolated yield for the methyl acrylate was about 30%. Thus, pyrolysis of 2a shows promise as a viable route to methyl acrylate.

Figure 4:
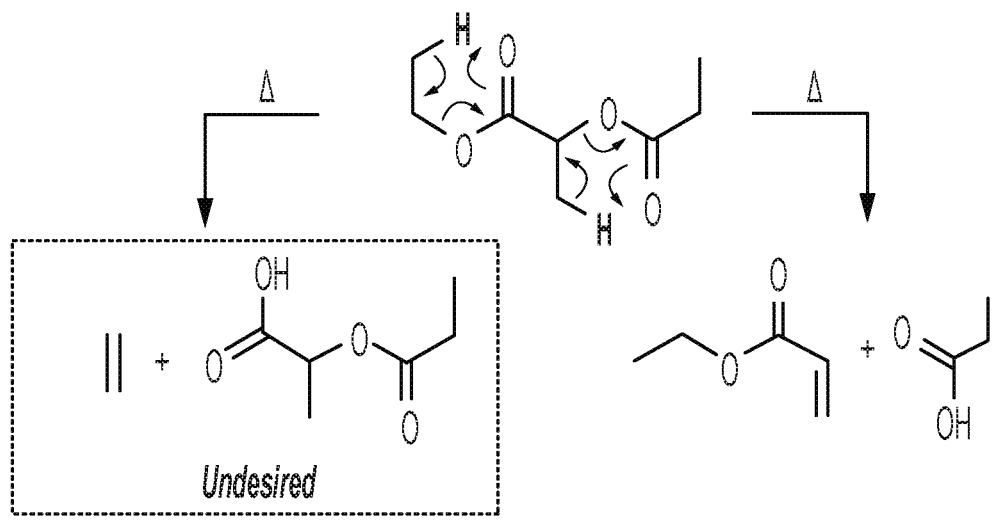
FIG. 4 shows pyrolytic decomposition pathways for 2b.
Figure 10:
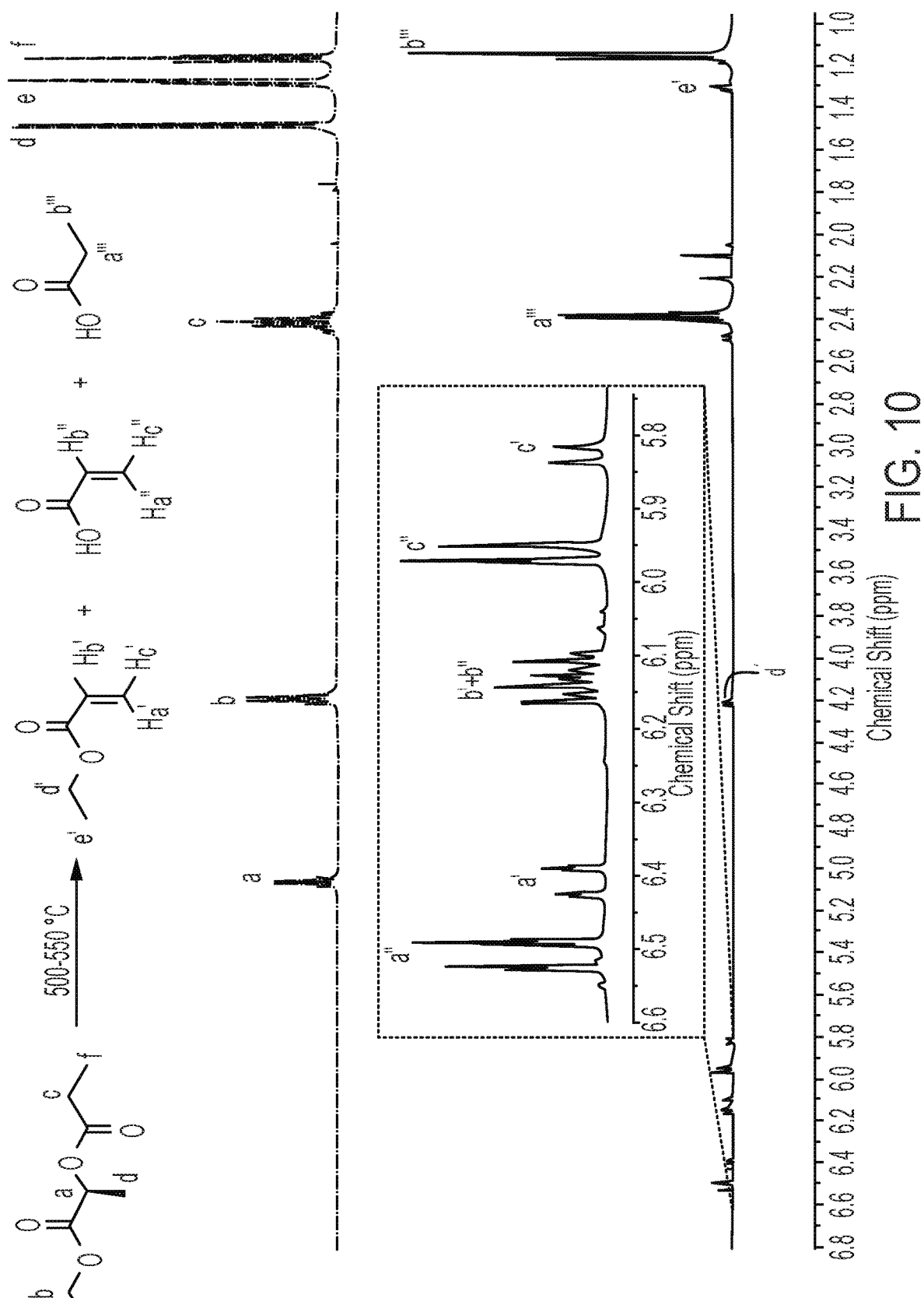
FIG. 10 shows $^1$H NMR spectrum of crude oil (bottom) obtained from the pyrolysis of ethyl 2-(propionyloxy)propanoate (top, starting material). The inset of the crude oil shows the vinylic protons of ethyl acrylate and acrylic acid.

Similarly, pyrolysis of ethyl 2-(propionyloxy)propanoate 2b gave ethyl acrylate, albeit in much lower yield, in line with previous studies of the corresponding acetoxy ester. The $^1$H NMR spectrum of the isolated product also showed the presence of acrylic acid (FIG. 10). FIG. 4 shows the pyrolytic decomposition mechanism of 2b which suggests that the presence of H-atoms beta to the ester O-atom may play a role in facilitating competitive elimination at the lactate ester over the acetoxy ester (Burns, R. et al, *J. Chem. Soc.* (1935) 400-406; Rehberg, C. E. et al, *J. Am. Chem. Soc.* (1945) 67:56-57)

EXAMPLES

Materials and Methods

Solvents and reagents were purchased from Sigma Aldrich, STREM, and Oakwood Chemicals, and used without further purification unless otherwise noted. Acetonitrile was stirred over activated alumina (neutral) and filtered prior to use. Methyl and ethyl lactate were distilled and stored over 4 Å molecular sieves prior to use. Gas chromatography, flame ionization detection (GC-FID) was performed using an Agilent 7890 series gas chromatograph system (HP-5 column, 30 m length, 0.32 mm ID, 0.25 μm (micron) film thickness; temperature program: 50° C. for 1.5 min, 15° C./min to 290° C., hold 5 min) equipped with a POLYARC® reactor (Activated Research Co.) for quantitative carbon detection (Maduskar, S. et al, J. Lab Chip 2015, 15, 440-447). $^1$H NMR spectra were recorded on Varian INOVA® 500 MHz, Bruker AVANCE® III 500 MHz, Bruker AVANCE® III HD 500 MHz, or Bruker AVANCE® III HD 400 MHz spectrometers. Chemical shifts are reported with respect to tetramethylsilane (TMS). Methyl and ethyl 2-acetoxypropanoates (Smith, L. T. et al, *Ind. Eng. Chem.* (1942) 34:473-479; Rehberg, C. E. et al, *J. Am. Chem. Soc.* (1945) 67:56-57), as well as $Pd(OTs)_2(MeCN)_2$ (Drent, E. et al, *J. Organomet. Chem.* (1991) 417:235-251) were prepared according to previously reported procedures.

Example 1 General Procedure for the Catalytic Hydroesterification of Alkyl Lactate II to Form Alkyl 2-(Propionyloxy)Propanoate I A 3 oz. (about 88.7 mL) Fisher-Porter bottle and apparatus was charged with all solid reagents, including palladium catalyst, organic acid, and ligand, and a stir bar, and sealed. The vessel was pressurized and vented four times with carbon monoxide, CO (160 psig) before solvent (2 mL) and alkyl lactate (1 mL, 10.47 mmol methyl lactate or 8.72 mmol ethyl lactate) were added via syringe. The vessel was once again pressurized and vented four times with carbon monoxide, CO (160 psig) and then ethylene gas, $C_2H_4$ (80 psig). Finally, the vessel was pressurized with $C_2H_4$ (80 psig) and CO (80 psig, total P=160 psig), and heated in oil bath with stirring for the allotted reaction time. The reaction vessels were then removed from heat, and vented to air, after which they were allowed to cool. Reaction mixtures were quantitatively transferred to 10 mL volumetric flasks and diluted with ethyl acetate. A 0.1 mL aliquot of this solution was then transferred to a 10 mL volumetric flask along with 0.1 mL of a 1,3,5-trimethoxybenzene standard (about 0.119 M), before being diluted to the mark with ethyl acetate and filtered through a small plug of silica gel to remove Pd and TsOH. The solutions were immediately analyzed by GC-FID. Peak areas were converted to concentrations by comparison to trimethoxybenzene (TMB), which itself was quantified by comparison to calibration data. Conversion from TMB concentration to analyte concentration was done using the following formula:

$$[Analyte] = [Standard]\left(\frac{\#Carbon_{TMB}}{\#Carbon_{analyte}}\right)\left(\frac{PeakArea_{analyte}}{PeakArea_{TMB}}\right)$$

Example 2 General Procedure for the Pyrolysis of Alkyl 2-(Propionyloxy)Propanoate The pyrolysis apparatus used was based on those previously described (Smith, L. T. et al, *Ind. Eng. Chem.* (1942) 34:473-479; Rehberg, C. E. et al, *J. Am. Chem. Soc.* (1945) 67:56-57) and consisted of a volatilization segment, a pyrolysis segment, and a condensation segment. Substrate was injected into a 100 mL 2-necked round bottom flask through a rubber septum and carried through the apparatus using $N_2$ as the carrier gas. The injection flask was packed with pyrex beads and submerged in a sand bath heated at ~250° C. The flask was connected via ground glass joints to a pyrex or quartz tube that was heated to ~500-550° C., and this glass connection was heated to ~250° C. with heating mantle tape. The pyrolysis tube was heated using an electric tube furnace, and the heated section was approximately 30 cm in length. The tube extended out beyond the tube furnace and was connected to a reflux condenser which was cooled at 0° C. with a chiller. This condenser fed into a 2-necked round bottom flask which was cooled in a dry-ice isopropanol bath and connected to another flask, also cooled in a dry-ice/isopropanol bath. The final flask was fit with an oil bubbler, to ensure neutral pressure differential throughout the setup, and to protect from the atmosphere. In a typical run, 5 mL of alkyl 2-(propionyloxy)propanoate of formula II were slowly injected dropwise into the initial round bottom flask, either by hand or using a syringe pump. The reaction was allowed to run for ~10 min post injection of substrate, after which heating was stopped and the collected product was analyzed by $^1H$ NMR spectroscopy. The collected products, including an acrylate ester of formula III, acrylic acid and propionic acid, from these reactions generally condensed exclusively in the first cooled flask or farther up the apparatus.

Figure 8:
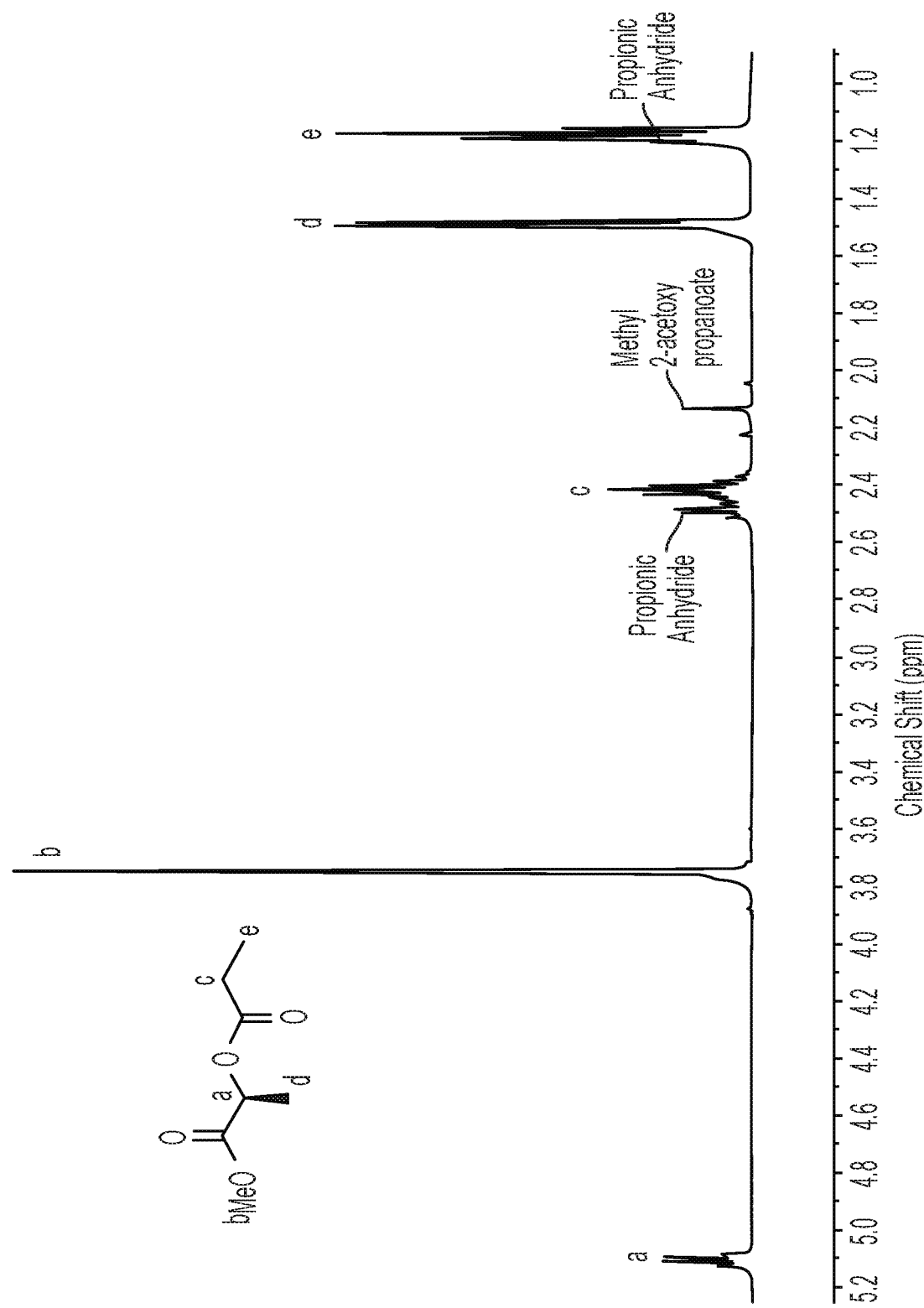
FIG. 8 shows $^1$H NMR spectrum (400 MHz, $CDCl_3$) of crude distillate shown above in FIG. 7A, which is consistent with the desired product, methyl 2-(propionyloxy)propanoate 2a and propionic anhydride.

Example 3 Synthesis of Methyl 2-(Propionyloxy)Propanoate 2a as a Standard Reference To a 100 mL round bottom flask equipped with a stir bar, 25.0 mL (27.3 g, 262 mmol) of (−)-methyl L-lactate were added, and the flask was fit with a pressure equalizing addition funnel and cooled in an ice bath. Propionic anhydride (37.5 g, 36.8 mL, 288 mmol) was added to the addition funnel, along with 0.1 mL of concentrated $H_2SO_4$ (aq). The solution was slowly added dropwise with stirring, resulting in a slight warming of the solution. Once the addition was complete, the reaction was allowed to stir at room temperature for 2-3 hrs, after which $K_2CO_3$ was added in portions until no more bubbling was observed. The solution was filtered and the white precipitate was washed with ethyl acetate. The resulting organic solution was washed with saturated sodium carbonate (2×10 mL) and brine (2×10 mL) before being collected and dried over anhydrous $Na_2SO_4$. Upon removal of solvent, a viscous colorless oil was obtained (33.7 g, 80.2%). The $^1H$ NMR spectrum is consistent with the previously published spectrum (Rioz-Martínez, A. et al, *Angew. Chem., Int. Ed.* (2011) 50:8387-8390). See FIG. 8 for representative spectrum. $^1H$ NMR (500 MHz, CDCl3): δ 5.10 (q, 1H), 3.75 (s, 3H), 2.43 (m, 2H), 1.48 (d, 3H), 1.17 ppm (t, 3H).

Example 4 Synthesis of Ethyl 2-(Propionyloxy)Propanoate 2b as a Standard Reference To a 100 mL round bottom flask equipped with a stir bar, 25.0 mL (25.8 g, 218 mmol) of (−)-ethyl L-lactate were added, and the flask was fit with a pressure equalizing addition funnel and cooled in an ice bath. Propionic anhydride (31.2 g, 30.6 mL, 240 mmol) was added to the addition funnel, along with 0.1 mL of concentrated $H_2SO_4$ (aq). The solution was slowly added dropwise with stirring, resulting in a slight warming of the solution. Once the addition was complete, the reaction was allowed to stir at room temperature for 2-3 hrs, after which $K_2CO_3$ was added in portions until no more bubbling was observed. The solution was filtered and the white precipitate was washed with ethyl acetate. The resulting organic solution was washed with saturated sodium carbonate (2×10 mL) and brine (2×10 mL) before being collected and dried over anhydrous $Na_2SO_4$. Upon removal of solvent, a viscous colorless oil was obtained (26.1 g, 68.7%). The $^1H$ NMR spectrum is consistent with the previously published spectrum (Geraghty, N. W. A. et al, *Tetrahedron* (2011) 67:3546-3552). $^1H$ NMR (500 MHz, CDCl3): δ 5.05 (q, 1H), 4.18 (q, 2H), 2.41 (m, 2H), 1.46 (d, 3H), 1.25 (t, 3H), 1.15 ppm (t, 3H).

Although the foregoing has been described in some detail by way of illustration and example for purposes of clarity of understanding, the descriptions and examples should not be construed as limiting the scope of the present disclosure. Accordingly, all suitable modifications and equivalents may be considered to fall within the scope of the present disclosure as defined by the claims that follow. The disclosures of all patent and scientific literature cited herein are expressly incorporated in their entirety by reference.

What is claimed is:

1. A process for the preparation of an alkyl 2-(propionyloxy)propanoate of formula I:

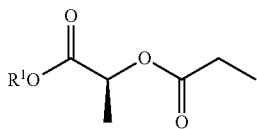

or a salt thereof, the process comprising contacting an alkyl lactate of formula II:

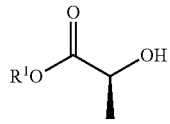

or a salt thereof, with carbon monoxide, ethylene, a phosphine reagent, and a palladium compound under conditions sufficient to form an alkyl 2-(propionyloxy)propanoate of formula I;
wherein $R^1$ is selected from H, $C_1$-$C_{12}$ alkyl, and $C_6$-$C_{20}$ aryl, where alkyl and aryl are optionally substituted with one or more groups independently selected from F, Cl, Br, I, —CN, —$NH_2$, —$NHCH_3$, —$N(CH_3)_2$, —$NHS(O)_2CH_3$, —$NO_2$, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, and —$S(O)_3H$;
the palladium compound is selected from $Pd(OAc)_2$, $Pd(OTs)_2(MeCN)_2$, $Pd(OCOCF_3)_2$, $Pd(BF_4)_2(MeCN)_2$, $Pd(BAr^F_4)_2(MeCN)_2$, $Pd(PF_6)_2(MeCN)_2$, $PdX_2$ where X is Cl, Br, or I, and $Pd(OTf)_2(MeCN)_2$; and
the phosphine reagent is selected from the group consisting of triphenylphosphine, P(t-Bu)$_3$, P(o-Tol)$_3$, dppf, and dppe.

2. The process of claim 1 wherein $R^1$ is selected from the group consisting of H, methyl, ethyl, and phenyl.

3. The process of claim 1 wherein the palladium compound is $Pd(OAc)_2$.

4. The process of claim 1 wherein the alkyl lactate of formula II, carbon monoxide, ethylene, and palladium compound are contacted at a pressure in the range of 14.7 to 1000 psig of carbon monoxide.

5. The process of claim 1 wherein the alkyl lactate II, carbon monoxide, ethylene, and a palladium compound are at a pressure in the range of 14.7 to 1000 psig of ethylene.

6. The process of claim 1 wherein the alkyl lactate II, carbon monoxide, ethylene, and a palladium compound are at a total pressure in the range of 29.4 to 2000 psig.

7. The process of claim 1 wherein the conditions of contacting the alkyl lactate II with carbon monoxide, ethylene, and a palladium compound are at a temperature in the range of 20 to 150° C.

8. The process of claim 1 wherein the conditions of contacting the alkyl lactate II with carbon monoxide, ethylene, and a palladium compound further comprises a solvent selected from toluene, DMF, acetonitrile, THF, ethyl acetate, nitromethane, N-methyl pyrrolidinone, and 2-MeTHF.

9. The process of claim 8 wherein the solvent is selected from toluene, THF, and ethyl acetate.

10. The process of claim 1 wherein the conditions of contacting the alkyl lactate II with carbon monoxide, ethylene, and a palladium compound do not include a solvent.

11. The process of claim 1 wherein the conditions of contacting the alkyl lactate II with carbon monoxide, ethylene, and a palladium compound further comprises a phosphine reagent.

12. The process of claim 11 wherein the phosphine reagent is triphenylphosphine.

13. The process of claim 1 wherein the conditions of contacting the alkyl lactate II with carbon monoxide, ethylene, and a palladium compound further comprises an organic acid selected from para-toluene sulfonic acid, methanesulfonic acid, trifluoromethane sulfonic acid, acetic acid, and trifluoroacetic acid.

14. The process of claim 13 wherein the organic acid is para-toluene sulfonic acid.

15. The process of claim 1 wherein the conditions of contacting the alkyl lactate II with carbon monoxide, ethylene, and a palladium compound further comprises an inorganic acid selected from hydrochloric acid, sulfuric acid, tetrafluoroboric acid, hexafluorophosphoric acid, and tetrakis(bis(3,5-trifluoromethyl)phenyl)boric acid.

16. The process of claim 1 further comprising heating the alkyl 2-(propionyloxy)propanoate ester of formula I or a salt thereof, to form an acrylate ester or acid of formula III:

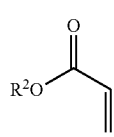

or a salt thereof, wherein $R^2$ is selected from H, $C_1$-$C_{12}$ alkyl, and $C_6$-$C_{20}$ aryl, where alkyl and aryl are optionally substituted with one or more groups independently selected from F, Cl, Br, I, —CN, —$NH_2$, —$NHCH_3$, —$N(CH_3)_2$, —$NHS(O)_2CH_3$, —$NO_2$, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$S(O)_2CH_3$, and —$S(O)_3H$;
and propionic acid or a salt thereof.

17. The process of claim 16 wherein $R^2$ is selected from the group consisting of H, methyl, ethyl, and phenyl.

18. The process of claim 16 wherein the alkyl 2-(propionyloxy)propanoate ester of formula I is heated in a heating unit wherein the heating unit is heated in a range of 450 to 600° C.

19. The process of claim 16 wherein the alkyl 2-(propionyloxy)propanoate ester I is passed through the inlet of the heating unit and exited into a collector vessel, wherein the heating unit is heated at about 500° C.

20. The process of claim 19 wherein the alkyl 2-(propionyloxy)propanoate ester I is passed through the heating unit with a carrier gas selected from the group consisting of nitrogen, argon, helium, and carbon dioxide.

21. The process of claim 18 wherein the heating unit is a pyrex glass or quartz tube.

22. The process of claim 19 wherein the collector vessel is cooled below ambient temperature.

23. The process of claim 18 wherein the alkyl 2-(propionyloxy)propanoate ester I is heated in the heating unit for about one second to about 45 seconds.

\* \* \* \* \*

UNITED STATES PATENT AND TRADEMARK OFFICE
CERTIFICATE OF CORRECTION

PATENT NO. : 10,710,956 B2  
APPLICATION NO. : 16/270351  
DATED : July 14, 2020  
INVENTOR(S) : Ian A. Tonks, Marc A. Hillmyer and Gereon M. Wuu-Yee It is certified that error appears in the above-identified patent and that said Letters Patent is hereby corrected as shown below:

In the Claims

Column 16, Lines 52-53, Claim 18, please delete "—$S(O)_2N(CH_3)_2$, —$S(O)_2CH_3$" and insert -- $S(O)_2N(CH_3)_2$, —$SCH_3$, —$S(O)_2CH_3$ -- therefor.

Signed and Sealed this  
Twenty-third Day of February, 2021

Drew Hirshfeld  
*Performing the Functions and Duties of the*  
*Under Secretary of Commerce for Intellectual Property and*  
*Director of the United States Patent and Trademark Office*